United States Patent [19]

Öberg

[11] Patent Number: 4,821,200

[45] Date of Patent: Apr. 11, 1989

[54] METHOD AND APPARATUS FOR MANUFACTURING A MODIFIED, THREE-DIMENSIONAL REPRODUCTION OF A SOFT, DEFORMABLE OBJECT

[75] Inventor: Kurt Öberg, Jönköping, Sweden

[73] Assignee: Jonkopings Lans Landsting, Jonkoping, Sweden

[21] Appl. No.: 34,228

[22] Filed: Apr. 2, 1987

[30] Foreign Application Priority Data

Apr. 14, 1986 [SE] Sweden ............................. 8601671

[51] Int. Cl.$^4$ ..................... G06F 15/46; G06G 7/64
[52] U.S. Cl. .......................... 364/474.24; 364/190; 364/167.01; 356/376; 425/2
[58] Field of Search ............... 364/474, 475, 556, 168, 364/413, 414, 190, 167, 822; 433/214; 425/2; 356/376

[56] References Cited

U.S. PATENT DOCUMENTS

| | | | |
|---|---|---|---|
| 4,089,608 | 5/1978 | Hoadley ............................. | 356/376 |
| 4,146,926 | 3/1979 | Clerget et al. ..................... | 364/556 |
| 4,575,805 | 3/1986 | Moermann et al. ................ | 364/168 |
| 4,611,288 | 9/1986 | Duret et al. ........................ | 364/474 |
| 4,663,720 | 5/1987 | Duret et al. ........................ | 433/214 |
| 4,697,240 | 9/1987 | Cedar et al. ........................ | 364/168 |

Primary Examiner—Jerry Smith
Assistant Examiner—P. Gordon
Attorney, Agent, or Firm—Cohen, Pontani & Lieberman

[57] ABSTRACT

The invention relates to a method of producing a reproduction of an object and an apparatus for carrying out said method. A particular object of the invention is the reproduction of the remaining stump of an amputated leg (18) for producing an improved prosthetic socket. When carrying out the method, the object (18) is positioned in a predetermined position in relation to a rotatable framework (8) on which a laser apparatus (12) and a video camera (13) are mounted in such positions that they can illuminate, and pick up, respectively, the image of a contour line (17) of the object via a pair of mirrors (15, 16; 20, 21) each during the rotation of the framework (8) through substantially a complete revolution. The image thus obtained of the contour line (17) is converted through a video/AD-converter (26) into numerical information identifying coordinates of points on the line. This information is supplied together with measuring and control programs to a computer (27), the output signals of which are supplied as input signals to a control electronic unit. The output signals from the electronic units control a model milling cutter in such a way that this on a workpiece produces a contour line which corresponds to a modified form of the contour lines of the object. The framework (8) with laser apparatus (12) and video camera (13) is intermittently rotated stepwise a predetermined fraction of a revolution, and for each step the abovementioned measures are repeated until the framework has been rotated through a complete revolution.

12 Claims, 3 Drawing Sheets

METHOD AND APPARATUS FOR MANUFACTURING A MODIFIED, THREE-DIMENSIONAL REPRODUCTION OF A SOFT, DEFORMABLE OBJECT

BACKGROUND OF THE INVENTION

This invention relates generally to a method of producing a modified, three-dimensional reproduction of an object, as well as to an apparatus designed for carrying out this method.

A special field of use in which the invention can be utilized is the manufacture of prosthetic sockets. Such prosthetic sockets, which are fitted, e.g. on the residual stump of an amputed leg or an amputed arm, have to have excellent fitting properties not to cause the amputee discomfort or suffering.

When manufacturing such prosthetic sockets one has hitherto proceeded in such a way that one has made a cast of the leg stump (or corresponding limb) in a plaster bandage or the like and thereby obtained a female model of the leg stump. Of this female model there is subsequently made a male replica of the female plaster cast. The shape of this male replica is then modified in conformity with the shape of the leg stump in its loaded condition, and subsequently there is made with the aid of the lastmentioned model a prosthetic socket which conforms to the shape of the model in its loaded condition.

SUMMARY OF THE INVENTION

The above method is circumstantial and time consuming and leads in many cases to less satisfactory results. In view of the above the principal object of the invention resides in providing a method and an apparatus of the abovementioned kind by means of which all sorts of objects, particularly the residual stump of an amputed arm or an amputed leg can be reproduced, the reproduction in the above special case subsequently being utilized as a model for manufacturing an improved prosthetic socket.

This object is attained thanks to the fact that the method and the apparatus according to the invention are carried out as defined in the characterizing clause of claims 1 and 2, respectively.

When leg prosthetics and the like are concerned, the leg stump introduced into the prosthetic socket is loaded when one stands or walks on the prosthesis. According to a special feature of the invention the shape of the reproduction or model is modified in such a way that it obtains the same shape as the leg stump gets when being loaded at walking.

Further features and advantages of the method and the apparatus according to the invention will become apparent from the following detailed description and the annexed drawings which diagrammatically and as non-limiting examples illustrate an apparatus for the manufacture of a replica or model of an ampute's leg stump remaining after an amputation.

DESCRIPTION OF THE PREFERRED EMBODIMENT

Figure 1:
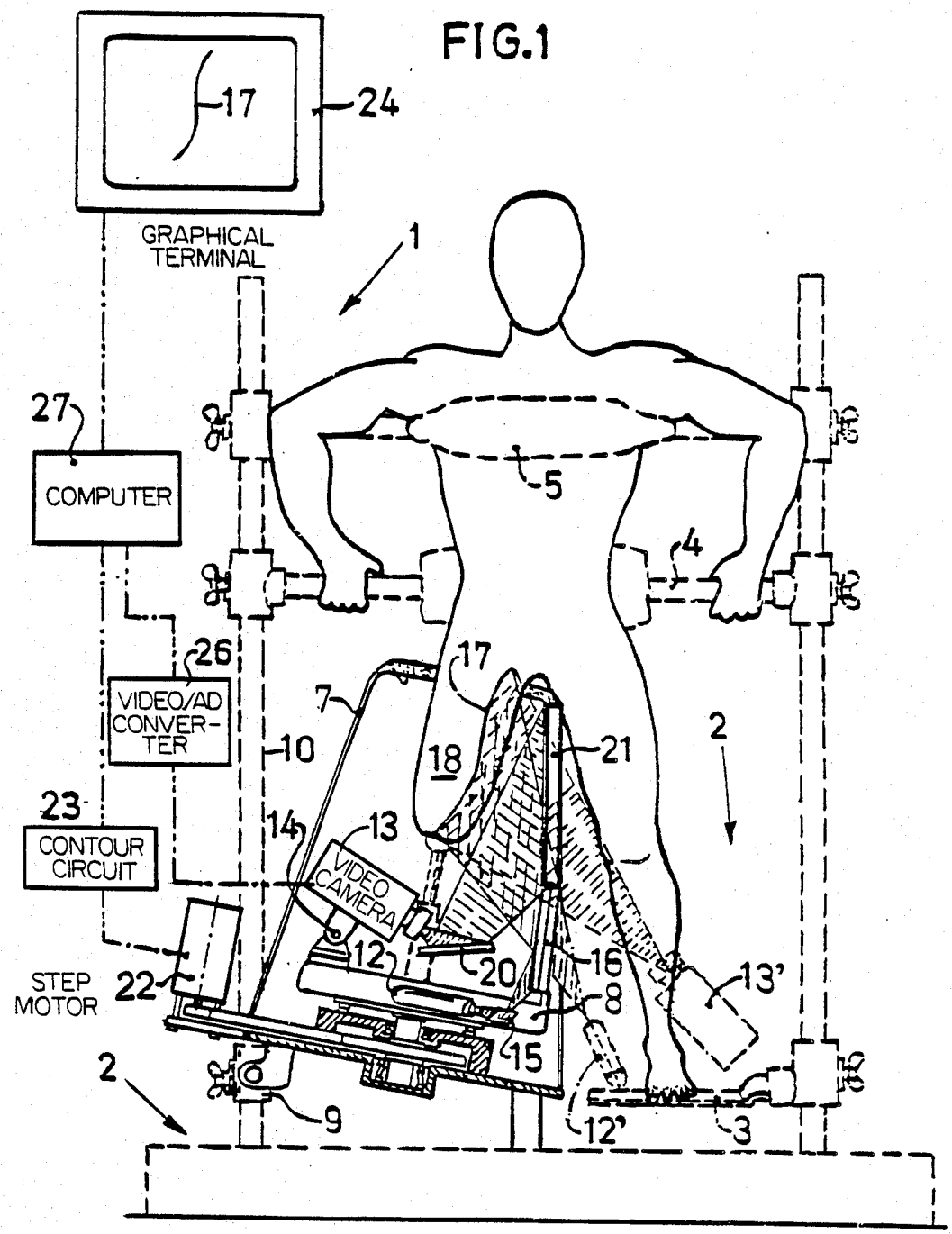
FIG. 1 illustrates diagrammatically a measuring apparatus comprised in the apparatus according to the invention and being illustrated as designed specially for the measuring of a leg stump.

To the measuring apparatus shown in FIG. 1 and generally designated 1 belongs a stand which is indicated in dash lines and is generally designated 2. This stand comprises a platform 3 on which a person having an amputed leg stands on his other leg, a pair of arm and waste supports 4, which are seized by the person with his hands, and a chest belt 5, by means of which the upper part of the body of the person is maintained fastened. By means of the stand 2 the person occupies a comparatively exactly fixed position.

In an inclined, upwards substantially open shell 7, having more or less open walls there is provided a rotatable framework 8. The inclination of the shell may be adjusted by means of a sleeve 9 which slidably surrounds a leg 10 comprised in the stand 2 and to which the sleeve can be screwed on.

A laser apparatus with line optics 12 and a video camera 13 are fixed to the framework 8. At least the camera 13 is adjustable and securable in selected positions, which in FIG. 1 is indicated through a horizontal axis of rotation 14. To the laser apparatus 8 there belongs two mirrors 15 and 16, which are so arranged that they together project the essentially plane bunch of rays generated by the laser apparatus on a curved contour line 17 of the leg stump 18 of the person which remains after the leg amputation. This stump is substantially enclosed in the shell 7. In the same way the camera 13 is coordinated with two further mirrors 20 and 21, which together direct the rays from the contour line 17 illuminated by the laser apparatus 12 towards the optics of the camera 13, so that the optical axis of the camera 13 sees the contour line 17 at a certain angle comprised between 20° and 70°, preferably about 45°, in the plane of rotation. The virtual positions of the laser apparatus and the camera, respectively, are indicated by dash lines and are designated 12' and 13', respectively, the hatched surfaces in FIG. 1 designate the ray bunches laser apparatus—leg stump—camera and are valid in respect of the real as well as the imaginary positions of the laser apparatus and the camera.

The framework 8 with the laser apparatus 12 and the video camera 13 may be rotated stepwise one revolution by means of a (step)motor 22. Each step comprises an angle of rotation which preferably is comprised between 1° and 5° A preferred angle is 1/100 revolution. The measuring course and the intermittent rotation of the framework 8 is controlled by a block-diagrammatically indicated computer 27 which is coupled to the step motor 22 via a control circuit 23 and to the video camera 13 via a video/analog-digital-converter 26 and which in the preferred embodiment also displays the contour line 17 captured by the video camera on a viewing screen or graphical terminal 24 which belongs to the computer and in which the line is designated 17'.

Figure 2:
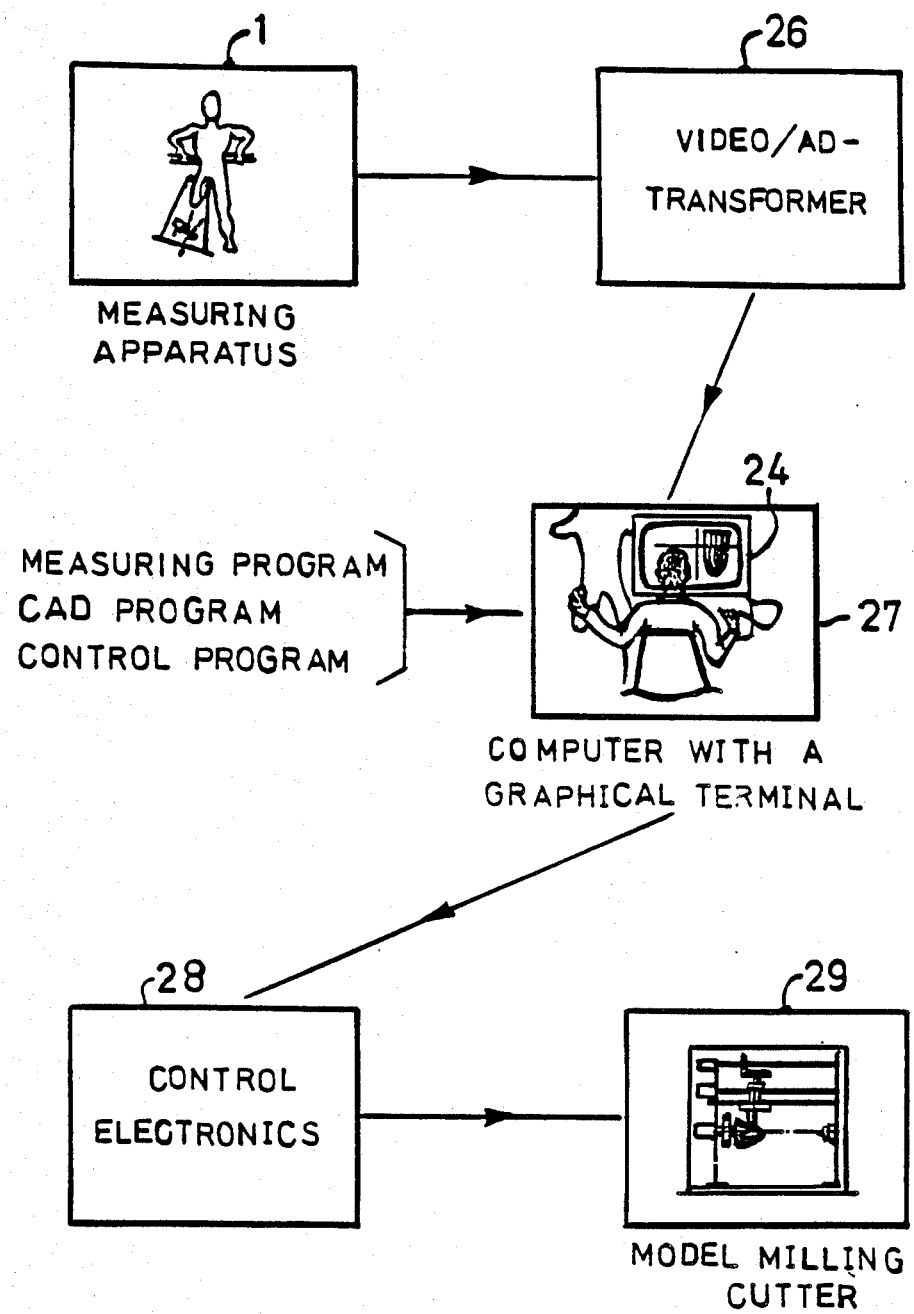
FIG. 2 is a block diagram of the components comprised in the apparatus according to the invention.

FIG. 2 is a block diagram of the principal components comprised in the apparatus according to the invention and illustrate the sequence of operation when carrying out the method according to the invention. In the block diagram there is comprised the measuring apparatus according to FIG. 1, a video/AD-converter 26, a computer 27 having a graphical terminal 24, a control electronic unit 28 and a model milling cutter 29.

The video/AD-converter 26 is fed with signals from the video camera 13 in FIG. 1 and converts the graphical representation 17 to coordinates for a predetermined number of points on each contour line 17, which constitute input data to the computer. The contour line 17 is converted into a 90° profile in the computer by means of trigonometric program. The cylindrical space coordinates v, x, y may represent the angle of rotation of the framework 8, counted from a predetermined initial position, the distance of the point from the axis of rotation of the framework and the distance of the point from a determined place which is perpendicular to the axis of rotation.

The measuring program in the computer primarily reads the contour line and-governs the rotation of the framework 8 by the motor 22 and other functions at the carrying out of the measuring operation. Through the control program the computer governs the operation of the model milling cutter 29 via the electronic unit 28. By means of the CAD program one converts the reel contour line 17 into the corresponding contour which is calculated to come into existance when the leg stump is loaded in the prosthetic socket. The control electronic 28 is fed with control signals in conformity herewith so that the milling cutter 29 on the workpiece cuts a curve which conforms to the modified contour line.

Figure 3:
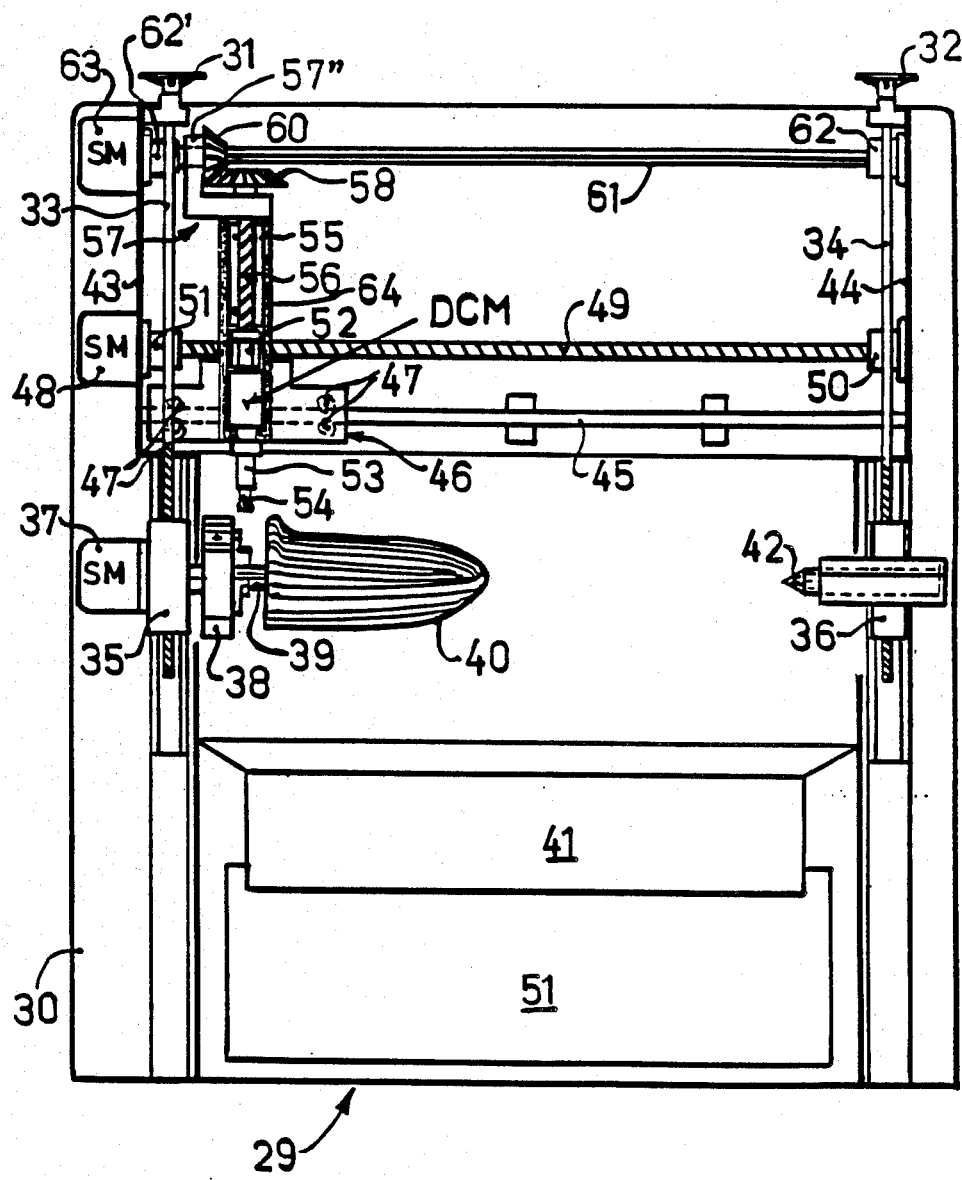
FIG. 3 is a diagrammatical view of a model milling cutter for the manufacture of the replica in question.

The model manufacturing apparatus 29 according to FIG. 3 is designed in the shape of a milling cutter. The apparatus comprises a framework which is generally designated 30 and in which two hand wheels 31, 32 each having a screw spindle 33 and 34, respectively, are rotatably journalled. Each screw spindle 33, 34 cooperates with an individual threaded sleeve 35 and 36, respectively. The sleeve 35 carries a step motor 37, a chuck 38 and a spindle 39 to which a model workpiece 40 is non-rotatably and non-displaceably secured in the illustrated exemplificatory embodiment. The threaded sleeve 36 carries a dowel 42 which is adjustable in its axial direction and is not used in the exemplificatory embodiment. The hand wheels 31, 32 and the screw spindles 33, 34 are utilized for positioning the spindle 39 and the dowel 42, respectively, into an initial or reference position.

Between two opposing walls 43, 44 of the framework 30 a horizontal rail 45 is affixed. A carriage 46 having two pairs of rotatably journalled rollers 47 is movable back and forth along the rail 45. A (step)motor 48 which is affixed to the wall 43 rotates a ball screw 49 which is journalled in bearings 50, 51 in the walls 44 and 43, respectively. The ball screw 49 which engages a ball nut 52 which is non-rotatably journalled on the carriage 46 displaces the carriage at the rotation of the motor 48. The carriage 46 carries a column tube 64 which is non-rotatably journalled in a ball bushing. In this tube there is mounted a direct current motor DCM, to the spindle of which a chuck 53 is secured, in which an end cutter 54 is inserted by means of which the model workpiece 40 is subjected to a chip removal at the rotation of the motor DCM in the illustrated exemplificatory embodiment.

As is apparent from the above the carriage 46 and together therewith the milling cutter 54 is translatorily or linearly movable in the horizontal direction. This is, however, not sufficient for milling or similar manufacture of a three-dimensional body of arbitrary shape. The column tube 64 and together therewith the milling cutter also have to be able to be displaced in the vertical direction, and to this end the column tube 64 is provided with a ball nut 55 having its balls in engagement with a ball screw 56 which is journalled in a bearing bracket which, is generally designated 57 and to the upper end of ball screw a bevel gear 58 is fixed above the bearing bracket 57 is fixed. This beveled gear 58 engages a second bevel gear 60 which internally is secured to a torque bushing and thereby is displaceably but non-rotatably secured to a shaft 61. The torque bushing is journalled in bearings 62 and 62' in the walls 44 and 43, respectively. The shaft 61 which passes with clearance through the bevel bearing bracket 57 can be rotated by means of a (step)motor 63 which is secured to the wall 43. When the motor 63 runs, the shaft 61 and the ball screw 56 are rotated, independently of where along the rail 45 the carriage 46 is, whereby the carriage 46 and the milling cutter 54 are raised or lowered.

In dependence of the control program by which the computer 27 is fed, there is thus milled in the model workpiece 40 a trace or a contour line which conforms to or corresponds to the contour line 17 of the leg stump 18 or an object corresponding hereto. The milling cutter 54 is subsequently returned to its initial position ( to the left in FIG. 3), after which the model workpiece 40 is rotated one step (3,°6 in the exemplificatory embodiment) and the milling course is repeated. Alternatively, another contour line may instead be milled from the right to space the left. When reproduction of a thigh or the like is concerned which changes shape when loaded and for which a prosthetic socket is to be manufactured by the aid of the finished model 40, the contour lines milled or shaped, respectively, by the milling cutter 54 (or a corresponding tool) are modified in accordance with the CAD program as is mentioned above. Below the workpiece 40 and the dowel 42 there is shown a chip catcher 41 and a chip box 51 in FIG. 3.

The embodiment described above and illustrated on the drawings is of course to be regarded merely as a non-limiting example and may as to its details be modified in several ways within the scope of the following claims. In particular the invention is not limited to the manufacture of replicas of parts of the body, such as arm stumps and leg stumps, in connection with the manufacture of prosthetic sockets. In addition to arm stumps and leg stumps and other parts of the body, e.g. torsos, rigid objects may be reproduced according to the invention. In the last mentioned case no CAD program is required for modifying the contour lines 17 which are illuminated by the laser apparatus 12 and are to be milled or manufactured in another way of the model, if not a modified shape of the model is to be made.

What I claim is:

1. Method of producing a modified, three-dimensional reproduction of a soft, elastically deformable object, characterized by the following measures:
    (a) positioning the object in a predetermined position in respect of a rotatable framework on which a laser apparatus and a video camera are mounted to illuminate and receive, respectively, the image of a contour line of the object, via at least one mirror each, when the framework is rotated through one complete revolution;
    (b) intermittently rotating said framework stepwise to produce an analog signal based on the image recorded by said video camera for each step;
    (c) converting the image of the contour line thus obtained at each step through a video/AD-converter into numerical information identifying coordinates of points on the contour line;

(d) supplying said numerical information together with measuring and control programs to a computer, preferably having a graphical terminal;

(e) modifying said numerical information supplied to the computer according to the measuring program as modified according to a CAD program in agreement with a calculated deformation of the object on account of a precalculated load;

(f) applying the output signals from the computer as input signals to a control electronic unit;

(g) controlling by said control electronic unit a model manufacturing machine having tool in such a way that said tool on a work-piece produces a contour line which conforms to the modified contour line of the object for each step;

(h) continuing said intermittent rotation of the framework including laser apparatus and video camera stepwise through a predetermined fraction of a revolution until the framework has been rotated through at least almost one complete revolution; and (i) intermittently rotating the model workpiece stepwise in relation to the tool of the model manufacturing machine in the same way as the framework, is rotated in relation to the object, for producing a modified reproduction of the object.

2. Apparatus for the manufacture of a modified, three-dimensional reproduction of a soft, elastically deformable object, characterized by the combination of:

(a) a measuring apparatus having means for positioning the object in a predetermined position in relation to the surrounding space, and a framework which is rotatable at least almost through one revolution in relation to the object on which a laser apparatus and a video camera comprising video optics are mounted in such positions that they can illuminate and receive, respectively, the image of a contour line of the object via at least one mirror mounted on the framework;

(b) a video/AD-converter for converting the obtained image into numerical information identifying coordinates of points on said contour line;

(c) a computer connected to the converter for receiving said numerical information from the converter;

(d) means for generating a measuring program and a control program and for supplying these to the computer;

(e) means for generating a CAD program and supplying this to the computer for modifying said information introduced into the computer in accordance with the measuring program, in conformity with a calculated deformation of the object on account of a precalculated load;

(f) a control electronic unit connected to the computer;

(g) a model manufacturing unit which is coupled to the control electronic unit and has a tool for producing on a workpiece to be treated a contour line conforming to the modified contour line of the object in dependence of signals received from the control electronic unit;

(h) means for intermittent and stepwise rotation of the framework, including the laser apparatus and the camera positioned thereon, at least almost through a complete revolution for producing a succession of contour lines which together substantially reproduce the outer surface of the object; and (i) means for intermittent and stepwise rotation of the workpiece in relation to the model manufacturing unit in the same way as the framework has been rotated in relation to the object, for producing a modified reproduction of the object.

3. Apparatus according to claim 2, characterized in that the laser apparatus is coordinated with two mirrors, one of which is provided for receiving rays from the laser apparatus and reflect these towards the other mirror which in its turn is adapted to direct beams received from the first mirror towards the object in such a way that they illuminate a contour line of the object which is located substantially in the same plane as the axis of rotation of the framework.

4. An apparatus according to claim 3, characterized in that the object is comprised of a stump of an extremity remaining after an amputation.

5. Apparatus according to claim 2, characterized in that the video camera is coordinated with two mirrors, one of which is provided for reception of rays form a contour line of the object illuminated by the laser apparatus and reflect these towards the other mirror which in its turn is adapted to direct the rays received from the first mirror to the optics of the video camera.

6. An apparatus according to claim 5, characterized in that the object is comprised of a stump of an extremity remaining after an amputation.

7. Apparatus according to claim 2, characterized in that the video camera and the laser apparatus have geometrical axes which approximately are located in a common plane and intersect each other at an angle which is between 20° and 70°.

8. An apparatus according to claim 7, characterized in that the object is comprised of a stump of an extremity remaining after an amputation.

9. Apparatus according to claim 2, characterized by the provision of a viewing screen connected to the computer and adapted to reproduce each contour line of the object, illuminated by the laser apparatus and received by the video camera.

10. An apparatus according to claim 9, characterized in that the object is comprised of a stump of an extremity remaining after an amputation.

11. An apparatus according to claim 2, characterized in that the object is comprised of a stump of an extremity remaining after an amputation.

12. Apparatus according to claim 2, characterized in that the model manufacturing unit comprises:

(a) means for securing a model workpiece of which a modified model or reproduction of a soft, deformable object is to be produced;

(b) means for intermittent rotation of the workpiece in steps, each comprising only a few degrees, at least almost through a complete revolution;

(c) a machine having a cutting tool for removal of chips from the workpiece;

(d) a chuck or the like for the clamping of the tool;

(e) a motor for rotating the tool;

(f) means for displacing the chuck and the tool clamped therein back and forth along a first axial direction;

(g) means for displacing the chuck and the tool clamped therein in a second axial direction which is substantially perpendicular to the first direction; and (h) means for coordinated driving of said workpiece rotating means and said chuck displacing means in accordance with a predetermined program.

* * * * *